(12) United States Patent
Changoer et al.

(10) Patent No.: US 10,959,978 B2
(45) Date of Patent: *Mar. 30, 2021

(54) SUPPOSITORIES COMPRISING CANNABINOIDS

(71) Applicant: APIRx Pharmaceutical USA, LLC, New York, NY (US)

(72) Inventors: Lekhram Changoer, Ridderkerk (NL); George Anastassov, New York, NY (US)

(73) Assignee: APIRX Pharmaceutical USA, LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/710,183

(22) Filed: Dec. 11, 2019

(65) Prior Publication Data
US 2020/0108046 A1    Apr. 9, 2020

Related U.S. Application Data

(63) Continuation of application No. 16/122,079, filed on Sep. 5, 2018, now Pat. No. 10,543,190, which is a continuation of application No. 15/787,978, filed on Oct. 19, 2017, now Pat. No. 10,092,538.

(60) Provisional application No. 62/411,067, filed on Oct. 21, 2016.

(51) Int. Cl.
| | | |
|---|---|---|
| *A61K 31/352* | (2006.01) |
| *A61K 9/00* | (2006.01) |
| *A61K 9/02* | (2006.01) |
| *A61K 47/10* | (2017.01) |

(52) U.S. Cl.
CPC .......... *A61K 31/352* (2013.01); *A61K 9/0031* (2013.01); *A61K 9/02* (2013.01); *A61K 9/025* (2013.01); *A61K 47/10* (2013.01)

(58) Field of Classification Search
CPC .............................. A61K 31/352; A61K 9/02
See application file for complete search history.

(56) References Cited

U.S. PATENT DOCUMENTS 10,092,538 B2 * 10/2018 Changoer
10,534,190 B2 * 1/2020 Zhang \* cited by examiner

*Primary Examiner* — Savitha M Rao
*Assistant Examiner* — Gregg Polansky
(74) *Attorney, Agent, or Firm* — Swidler Law Group, LLC; Sean S. Swidler

(57) ABSTRACT

This invention relates to a suppository composition comprising cannabinoids. The suppository composition is formulated for easy absorption through mucosal membrane. The suppository as provided herein is useful for administration of cannabinoids in patients with nausea, vomiting, other conditions preventing swallowing, or conditions wherein suppository administration is required. Methods to manufacture the suppository composition are provided. Methods to treat pain, nausea, post-operative ileus and/or inflammatory bowel diseases using the suppository according to this invention are also provided.

12 Claims, No Drawings

SUPPOSITORIES COMPRISING CANNABINOIDS

CROSS-REFERENCE TO RELATED APPLICATIONS

This application is a continuation of U.S. application Ser. No. 16/122,079, filed Sep. 5, 2018, which is a continuation of U.S. application Ser. No. 15/787,978, filed Oct. 19, 2017, now U.S. Pat. No. 10,092,538 B2, which claims the benefit of U.S. Provisional Application No. 62/411,067, filed Oct. 21, 2016. Each of the above-referenced patent applications is incorporated by reference in its entirety.

BACKGROUND OF THE INVENTION

Field of the Invention

This invention relates to suppository formulations for medical use. The suppository may be applied to human cavities other than the oral cavity. This suppository provides efficient absorption of active ingredients while avoiding unpleasant taste and/or vomiting.

Description of the Related Technology

The *Cannabis* plant has many naturally occurring substances that are of great interest in the fields of science and medicine. Isolated compounds from the *Cannabis* plant include $\Delta^9$-tetrahydrocannabinol (THC), cannabidiol (CBD), cannabichromene (CBC), cannabigerol (CBG), cannabidivarin (CBDV), among other compounds. While THC has psychoactive effects, CBD, CBC, CBG, and CBDV do not. Isolated compounds from the *Cannabis* plant are called cannabinoids. There are a total of one hundred and forty one (141) cannabinoids that have been isolated from the *Cannabis* plant. Many researchers have confirmed the medicinal value of cannabinoids. Cannabinoids have been investigated for possible treatment of seizures, nausea, vomiting, lack of appetite, pain, arthritis, inflammation, and other conditions.

Cannabinoids can be isolated by extraction or cold pressing from *Cannabis* plants. Plants in the *Cannabis* genus include *Cannabis sativa, Cannabis ruderalis,* and *Cannabis indica*. These plants are natural sources of cannabinoids. Cannabinoids are also available in synthetic forms. Methods to synthesize cannabinoids in lab settings were discovered and are still currently practiced. Synthetic cannabinoids are more targeted, in that the synthetic compound usually comes isolated without other cannabinoids mixed in.

Nabilone (racemic(6aR,10aR)-1-hydroxy-6,6-dimethyl-3-(2-methyloctan-2-yl)-7,8,10,10a-tetrahydro-6H-benzo[c]chromen-9(6aH)-one), a synthetic cannabinoid, is believed to have fewer undesired side effects than THC. Nabilone mimics the chemical compound structure of THC. THC also exists in synthetic form under the name Dronabinol ((−)-(6aR,10aR)-6,6,9-trimythel-3-pentyl-6a,7,8,10a-tetrahydro-6H-benzo[c]chromen-1-ol)). These synthetic cannabinoids are sold for food supplement purposes and are being investigated for medicinal purposes. The U.S. Food and Drug Administration approved nabilone for treatment of chemotherapy-induced nausea and vomiting. In the United States, nabilone is marketed under the name Cesamet®.

The IUPAC nomenclature of THC is (−)-(6aR,10aR)-6,6,9-trimethyl-3-pentyl-6a,7,8,10a-tetrahydro-6H-benzo[c]chromen-1-ol. CBD's IUPAC nomenclature is 2-((1S,6S)-3-methyl-6-(prop-1-en-2-yl)cyclo-hex-2-enyl)-5-pentylbenzene-1,3-diol). CBC has the IUPAC nomenclature of 2-methyl-2-(4-methylpent-3-enyl)-7pentyl-5-chromenol. CBG has the IUPAC nomenclature of 2-[(2E)-3,7-dimethylocta-2,6-dienyl]-5-pentyl-benzene-1,3-diol. These are among the most prominent compounds in the family of compounds extracted from the *Cannabis* plant referred to as cannabinoids.

Cannabidiol is a major phytocannabinoid, accounting for up to 40% of the plant's extract. CBD is a CB-1 receptor antagonist, while THC is a CB-1 receptor agonist. A 2010 research found that *Cannabis* strains with higher concentration of CBD did not produce the short-term memory impairment normally seen in high THC *Cannabis* strains, a characteristic attributed to the CB-1 receptor antagonist nature of CBD. CBD is considered to have a wider scope of medical applications than THC.

Because it is a relatively unknown cannabinoid, cannabigerol (CBG) remains understudied and its effects are only just starting to become clear. CBG is a non-psychoactive cannabinoid found in the *Cannabis* plant. All cannabinoids in the early stage of the *Cannabis* plant's life begins as CBG. CBG is found in higher concentrations in hemp plants as opposed to marijuana plants, which are grown to have higher concentrations of tetrahydrocannabinol (THC). CBG has been found to act as a high affinity $\alpha_2$-adrenergic receptor agonist, a moderate affinity 5-HT$_{1A}$ receptor antagonist, and a low affinity CB$_1$ receptor antagonist. It binds with the CB$_2$ receptor, but it is currently unknown whether it acts as an agonist or antagonist.

*Cannabis* abuse can occur among chronic users, especially when raw plant materials are consumed by smoking. Collectively, this abuse is referred to as *Cannabis* use disorder. Discontinuance of *Cannabis* consumption can result in withdrawal symptoms. However, some cannabinoids, such as CBD, may be useful in treating *Cannabis* use disorder. Various methods to deliver CBD or other cannabinoids are available, aiming at avoiding inhalation of burning materials.

Suppository is a solid medical preparation in a roughly conical or cylindrical shape, designed to be inserted into the rectum or vagina to dissolve. Suppository may be used in administration of certain medications wherein administration via other routes is impractical, ineffective, or too invasive. Suppository is also preferred where the medication's action location is close to the rectum or the vagina and absorption through the mucosal membrane is effective. Suppository is also recommended when the active ingredient is easily degraded in gastric fluid or tastes too bad.

Suppository melts inside body cavities by the body's temperature and the presence of bodily fluid. Covers suitable for dissolution are gelatin or cocoa butter. Upon dissolution, active ingredients are absorbed through the mucosal membrane lining the body cavity.

SUMMARY

This invention provides a suppository composition comprising cannabinoids, a fatty base, a non-ionic surfactant, and a sugar alcohol or sugar. Cannabinoids may be CBD, CBG, CBN, THC, CBDV, or THCV, or a combination of all or some of these. Sugar alcohols may be isomalt, mannitol, sorbitol, xylitol, lactitol, maltitol, or erythritol. Sugars may be dextrose, maltose, fructose, or sucrose. Fatty bases may be ceteareth-15, glycerol ricinoleate, or hydrogenated cocoglycerin, among other suitable fatty bases, which may be sold under the brands Witepsol S58, Witepsol H15, or Witepsol H58. Non-ionic surfactants may be ceteareth-15, ceteareth-17, or ceteareth-25. Methods to manufacture and use the suppository composition are also provided.

This invention provides a suppository composition comprising:
at least one cannabinoid at 0.1% to 50% by weight of the total composition;
at least one sugar alcohol or sugar at 15% to 25% by weight of the total composition;
at least one fatty base suitable for suppository formulation at 60% to 80% by weight of the total composition; and
at least one non-ionic surfactant at 2% to 10% by weight of the total composition,
wherein the composition is packaged in a suppository mold.

The invention provides a suppository composition as above wherein the at least one cannabinoid is CBD, CBG, CBN, CBDV, and THCV.

The invention provides a suppository composition as above wherein the at least one cannabinoid is THC and wherein THC comprises 0.1% to 2% by weight of the total composition.

The invention provides a suppository composition as above wherein the at least one cannabinoid is from natural sources or synthetic.

The invention provides a suppository composition as above wherein the at least one cannabinoid is nanoencapsulated.

The invention provides a suppository composition as above wherein the particles are of size 20-40 nm.

The invention provides a suppository composition as above, wherein the at least one cannabinoid is encapsulated into hyaluronic acid derivatives nanolattice.

The invention provides a suppository composition as above, wherein the at least one cannabinoid is encapsulated into hyaluronic acid derivatives and tocopherol nanolattice.

The invention provides a suppository composition as above wherein the hyaluronic acid derivatives is sodium oleyl hyaluronate.

The invention provides a suppository composition as above, wherein the at least one sugar is selected from the group consisting of dextrose, maltose, fructose, and sucrose wherein the at least one sugar is provided in micronized form.

The invention provides a suppository composition as above, wherein the at least one sugar alcohol is selected from the group consisting of isomalt, mannitol, sorbitol, xylitol, lactitol, maltitol, and erythritol and wherein the at least one sugar alcohol is provided in micronized form.

The invention provides a suppository composition as above, wherein the at least one non-ionic surfactants may be selected from the group consisting of ceteareth-15, ceteareth-17, and ceteareth-25.

The invention provides a suppository composition as above, wherein the at least one fatty base is selected from the group consisting of ricinoleate, hydrogenated coco-glycerin, and ceteareth-25.

This invention provides a method to treat or alleviate nausea or vomiting, comprising administering the suppository according to claim 1 to a mammal 1-6 times a day as needed.

This invention provides a method to treat or alleviate nausea according to embodiments, wherein the nausea or vomiting is chemotherapy related nausea or vomiting.

This invention provides a method to treat or alleviate pain, comprising administering the suppository according to claim 1 to a mammal 1-6 times a day or as needed.

This invention provides a method to treat or alleviate pain according to embodiments, wherein the pain is menstrual pain.

This invention provides a method to treat or alleviate post-operative ileus, comprising administering the suppository according to claim 1 to a mammal 1-6 times a day or as needed.

This invention provides a method to treat or alleviate intestinal inflammation, comprising administering the suppository according to claim 1 to a mammal 1-6 times a day or as needed.

This invention provides a method to treat or alleviate intestinal inflammation according to embodiments, wherein the intestinal inflammation is irritable bowel syndrome or inflammatory bowel disease.

ABBREVIATIONS

CBC: Cannabichromene
CBD: Cannabidiol
CBDV: Cannabidivarin
CBG: Cannabigerol
CBN: Cannabinol
IUPAC: International Union of Pure and Applied Chemistry
THC: Tetrahydrocannabinol
THCV: Tetrahydrocannabidivarin

DETAILED DESCRIPTION OF CERTAIN INVENTIVE EMBODIMENTS

Embodiments of this application relate to a suppository composition comprising cannabinoids. Various cannabinoids may be incorporated into this suppository for effective absorption. Suppositories provide for absorption of active ingredients such as cannabinoids where oral application is ineffective, especially when the subject suffers from nausea or in uncooperative minors. A method to treat pain and nausea is also provided.

The word "cannabinoid" used in this description, claims, and other conjugations is used to mean any compound that interacts with a cannabinoid receptor and other cannabinoid mimetics, including, but not limited to, certain tetrahydropyran analogs ($\Delta^9$-tetrahydrocannabinol, $\Delta^8$-tetrahydrocannabinol, 6,6,9-trimythel-3-pentyl-6H-dibenzo[b,d]pyran-1-ol, 3-(1,1-dimethylheptyl)-6,6a7,8,10,10a-hexahydro-1-1hydroxy-6,6-dimythel-9H-dibezo[b,d]pyran-9-ol, (−)-(3S, 4S)-7-hy droxy-delta-6-tetrahydrocannabinol-1,1-dimethylheptyl, (+)-(3S,4S)-7-hydroxy-$\Delta$-6-tetrahydrocannabinol, and $\Delta^8$-tetrahydrocannabinol-11-oic acid); certain piperidine analogs (e.g., (−)-(6S,6aR,9R, 10aR)-5,6,6a,7,8,9,10,10a-octahydro-6-methyl-1-3-[(R)-1-methyl-4-phenylbutoxy]-1,9-phenanthridinediol 1-acetate)); certain aminoalkylindole analogs (e.g., (R)-(+)-[2,3-dihydro-5-methyl-3-(4-morpholinylm-ethyl)-pyrrolo[1,2,3,-de]-1,4-benzoxazin-6-yl]-1-naphthelenyl-methanone); certain open pyran-ring analogs (e.g., 2-[3-methyl-6-(1-methylethenyl-2-cyclohexen-1-yl]-5-pentyl-1,3-benzendiol, and 4-(1,1-dimethylheptyl)-2,3'-dihydroxy-6'-α-(3-hydroxypropyl)-1',-2',3',4',5',6'-hexahydrobiphenyl), their salts, solvates, metabolites, and metabolic precursors.

The word "cannabidiol" refers to cannabidiol and cannabidiol derivatives. As used in this application, cannabidiol is obtained from industrial hemp extract with a trace amount of THC or from *Cannabis* extract using high-CBD *Cannabis* cultivars. Alternatively, synthetic CBD may also be used.

The word "tetrahydrocannabinol" refers to tetrahydrocannabinol and tetrahydrocannabinol derivatives. As used in this application, tetrahydrocannabinol is obtained from *Cannabis* extract. Alternatively, synthetic THC may also be used.

The word "cannabigerol" refers to cannabigerol and cannabigerol derivatives. As used in this application, cannabigerol is obtained from industrial hemp extract or from *Cannabis* extract using high-CBG *Cannabis* cultivars with a trace amount of THC and other cannabinoids. Alternatively, synthetic CBG may also be used.

In embodiments, cannabinoids may be provided as crystallized cannabinoids in solid form. Solid cannabinoids may be obtained from natural sources by freeze drying and/or heating of *Cannabis* oil or hemp oil. Alternatively, solid cannabinoids may be obtained from synthetic sources. Methods to synthesize cannabinoids are disclosed in Patent Application Publication US2010/0298579 by THC Pharm GmbH and this reference is included herein as a whole.

Cannabinoids may also be in oily form, as *Cannabis* oil, hemp oil, or hashish oil. In these embodiments, emulsion formulation for the suppository content may have cannabinoids dispersed throughout the emulsion for better absorption. It is contemplated that cannabinoids provided in oily form may be used in the embodiments described herein.

In embodiments, cannabinoids may be procured from natural sources, where more than one cannabinoid may be present. Cannabinoids may also be procured from synthetic sources and a plurality of synthetic cannabinoids may be used in this suppository composition. At least one cannabinoid may be present in this suppository composition.

In embodiments, cannabinoids may also be provided in microencapsulation or nanoencapsulation form into particles. Encapsulation may result in cannabinoids and other materials present in cannabinoid materials in liposomal capsule particles or other types of particles.

Microencapsulation or nanoencapsulation may increase cannabinoid bioavailability by up to 4 times, thereby increasing cannabinoid efficacy after absorption through the mucosal membrane. Microencapsulation or nanoencapsulation may result in particles of 20-40 nm in size. Microencapsulation or nanoencapsulation promotes dissolution of cannabinoid particles in an aqueous environment.

In embodiments, cannabinoids may be nanoencapsulated into hyaluronic acid (HA) derivatives nanolattice. Additionally, cannabinoids may also be nanoencapsulated into a combination of hyaluronic acid derivatives and tocopherol nanolattice. Hyaluronic acid derivatives nanolattice may include but is not limited to sodium oleyl hyaluronate.

Cannabinoids as used in these embodiments may be CBD, CBG, CBN, THC, CBDV, THCV, or other molecules within the cannabinoid family. A combination of cannabinoids may be used in these embodiments, such that the total amount of cannabinoids comprises the quantities as described.

In embodiments, the suppository composition may comprise at least one cannabinoid, such as CBD, CBG, THC, derivatives thereof, or a combination of cannabinoids. Other cannabinoids suitable for use in this suppository composition may be CBN, CBDV, or THCV, or a combination thereof, among other cannabinoids.

In embodiments, the total amount of cannabinoids may be at 0.1% to 50% by total weight of the suppository composition. Total amount of cannabinoids may comprise different cannabinoids at different ratios. The total amount of THC may be at a lower weight percentage to minimize psychoactive effect.

The total amount of THC in embodiments may be at 0.1% to 2% by weight of the total composition. In a 2 gram suppository, THC may be at 2-40 mg. The total amount of cannabinoids other than THC may be at 0.1% to 5% by weight of the total composition. In a 2 gram suppository, cannabinoids other than THC may be at 2-100 mg. Where a combination of cannabinoids is used, total THC level may be between 0.1% to 2% by weight of the total composition and the total amount of all cannabinoids in a suppository composition may not exceed 50% by weight.

In embodiments, the suppository composition may comprise at least one water-soluble sugar alcohol or sugar. Suitable sugar alcohols may be isomalt, mannitol, sorbitol, xylitol, lactitol, maltitol, or erythritol. Suitable sugars may be dextrose, maltose, fructose, or sucrose. Sugar alcohol or sugar in these embodiments may comprise 15% to 25% by weight of the total composition. A combination of sugar alcohols and/or sugars may also be used. Sugar alcohols or sugars may be provided in micronized form to promote dissolution.

In embodiments, the suppository composition may comprise at least one fatty base of pharmaceutical grade for suppository formulations. Fatty bases may comprise fatty acids suitable for absorption through mucosal membranes, such as glycerol ricinoleate, hydrogenated coco-glycerin, and ceteareth-25. Fatty bases may be commercially available, such as Witepsol S58 sold by Cremer Health, or Witepsol H15, Witepsol H85, or other suitable fatty bases for suppository formulation.

Fatty bases for a suppository formulation as above may provide for a hydrophobic environment wherein cannabinoids may disperse. Apart from providing an environment for dispersion, fatty bases may also bulk up the formulation as a whole to provide for encapsulation in a suppository. Fatty bases in embodiments may comprise 60% to 80% by weight of the total composition. A combination of suitable fatty bases may also be used.

In embodiments, the suppository may further comprise at least one non-ionic surfactant to provide an emulsifier to promote equal dispersion of cannabinoids. Suitable non-ionic surfactants may be various ceteareth-n, which may be cetyl alcohol (ceteareth-15), stearyl alcohol (ceteareth-17), or ceteareth-25. Non-ionic surfactants may comprise 2% to 10% by weight of the total composition.

In embodiments, the suppository composition may be manufactured by first blending at least one cannabinoid in solid or liquid form with at least one non-ionic surfactant under a nitrogen blanket in a fluid bed reactor. A fluid bed reactor may cause the cannabinoids and non-ionic surfactant to behave as a liquid during manufacturing of the suppository formulation.

The manufacture process may further comprise spraying at least one non-ionic surfactant such as ceteareth-25 at about 50° C. into the cannabinoid-sugar alcohol or cannabinoid-sugar particles. Since the cannabinoid-sugar alcohol or cannabinoid-sugar particles are in the fluid bed reactor, the spraying also happens in this environment. The blend may then be cooled to room temperature while a $N_2$ stream is purged into the mixture.

A fatty base may be melted in a different vessel at about 70° C. in a separate vessel. Once melted, the cannabinoid-sugar alcohol or cannabinoid-sugar particles may be added into the vessel and the mixture may be stirred until homogenous while the mixture is kept at 70° C. The mixture may be continuously stirred while allowed to cool down.

The mixture from the step above may be poured into suppository molds before re-solidification. Upon closing of the suppository molds, the suppositories may be allowed to cool to room temperature. The suppositories may then be packed into air and moisture tight suppository blisters.

Suppositories may in conical, bullet, or round shape. A suppository may have an outside coating layer to promote dissolution by contact with the mucosal membrane and by the body's temperature. The outside coating layer may be by cocoa butter or gelatin from animal or plant sources.

In embodiments, the suppositories may be administered to a subject in need thereof by placing into cavities such as the rectum or the vagina. The suppositories may be held in the appropriate cavities for absorption until fully absorbed.

The suppository according to embodiments may be used in treatment or alleviation of nausea and/or vomiting. A mammal, such as a human being, may receive the suppository composition according to embodiments 1-6 times a day or as needed for nausea treatment.

The suppository according to embodiments may be used in treatment or alleviation of chemotherapy related nausea and vomiting. A mammal, such as a human being, may receive the suppository composition according to embodiments 1-6 times a day or as needed for treatment of chemotherapy related nausea and vomiting.

The suppository according to embodiments may be used in treatment or alleviation of pain and/or chronic pain. A mammal, such as a human being, may receive the suppository composition according to embodiments 1-6 times a day or as needed for pain treatment.

The suppository according to embodiments may be used in treatment or alleviation of menstrual cramps or pain. A mammal, such as a human being, may receive the suppository composition according to embodiments 1-6 times a day or as needed for menstrual cramp pain treatment.

The suppository according to embodiments may be used in treatment or alleviation of post-operative ileus. A mammal, such as a human being, may receive the suppository composition according to embodiments 1-6 times a day or as needed for treatment of post-operative ileus.

The suppository according to embodiments may be used in treatment or alleviation of intestinal inflammation such as irritable bowel syndrome (IBS), irritable bowel disease (IBD), such as ulcerative colitis and/or Crohn's disease. A mammal, such as a human being, may receive the suppository composition according to embodiments 1-6 times a day or as needed for treatment of intestinal inflammation such as IBS or IBD (Crohn's disease, ulcerative colitis).

EXAMPLES

Suppository Pill Preparation

A suppository having 20 mg of CBD is prepared. Percentages are given in weight percentage.

TABLE 1

| Phase | Raw Material | Percentage (%) |
| --- | --- | --- |
| A1 | Witepsol S58 | 70 |
| A2 | Ceteareth 25 | 5 |
| A3 | Hemp oil having CBD at 20% weight (nanoencapsulated) | 5 |
| A4 | Micronized isomalt | 20 |
|  | Total | 100 |

Witepsol S58 is obtained from IOI Olleochemical GmbH, having as its major components hydrogenated coco-glycerides, ceteareth-25, and glyceryl ricinoleate. Hemp oil having CBD at 20% weight and other minor amount of cannabinoids naturally occurring in hemp oil is nanoencapsulated.

Obtain ingredients according to the above percentage. Make a blend of Phase A3 and A4 under a nitrogen blanket in a fluid bed reactor. Spray Phase A2 at 50° C. on to the mixture above (cannabinoid—isomalt particles) in the fluid bed reactor. Cool the blend to room temperature while purging under nitrogen. Melt Phase A1 in a separate vessel at 70° C., and then add the mixture above into Phase A1. Stir the mixture at 70° C. until homogenous. Cool the mixture down while continuously stirring.

Before re-solidification, pour the mixture into suppository molds, and then cool the molds to room temperature. The suppositories may be of a mass of about 2 gram each. The suppositories may then be packed into air and moisture tight suppository blisters.

A suppository with a mass at about 2 gram and containing 20 mg CBD is prepared.

All references, including publications, patent applications, and patents cited herein are hereby incorporated by reference to the same extent as if each reference were individually and specifically indicated to be incorporated by reference and were set forth in its entirety herein.

It will be readily apparent to those skilled in the art that a number of modifications and changes may be made without departing from the spirit and the scope of the present invention. It is to be understood that any ranges, ratios, and range of ratios that can be derived from any of the data disclosed herein represent further embodiments of the present disclosure and are included as part of the disclosure as though they were explicitly set forth. This includes ranges that can be formed that do or do not include a finite upper and/or lower boundary. Accordingly, a person of ordinary skill in the art will appreciate that such values are unambiguously derivative from the data presented herein.

What is claimed is:

1. A method to treat intestinal inflammation, comprising: administering 1-6 times per day to a mammal a suppository composition comprising:
   at least one cannabinoid at 0.1% to 50% by weight of the total composition;
   at least one sugar alcohol or sugar at 15% to 25% by weight of the total composition;
   at least one fatty base suitable for suppository formulation selected from the group consisting of glycerol ricinoleate, hydrogenated coco-glycerin, and ceteareth-25 at 60% to 80% by weight of the total composition; and
   at least one non-ionic surfactant selected from the group consisting of ceteareth-15 and ceteareth-17 at 2% to 10% by weight of the total composition,
   wherein the at least one cannabinoid is nanoencapsulated into particles, and
   wherein the composition is packaged in a suppository mold.

2. The method of claim 1, wherein the cannabinoid is CBD, CBG, CBN, CBDV, or THCV.

3. The method of claim 1, wherein the at least one cannabinoid is THC and wherein THC comprises 0.1% to 2% by weight of the total composition.

4. The method composition of claim 1, wherein the at least one cannabinoid is from natural sources or synthetic.

5. The method of claim 1, wherein the particles are of size 20-40 nm.

6. The method of claim 1, wherein the at least one cannabinoid is encapsulated into hyaluronic acid derivative nanolattice, and wherein the hyaluronic acid derivative is sodium oleyl hyaluronate.

7. The method of claim 1, wherein the at least one sugar is selected from the group consisting of dextrose, maltose, fructose, and sucrose.

8. The method of claim 1, wherein the at least one sugar is provided in micronized form.

9. The method of claim 1, wherein the at least one sugar alcohol is selected from the group consisting of isomalt, mannitol, sorbitol, xylitol, lactitol, maltitol, and erythritol.

10. The method of claim 1, wherein the at least one sugar alcohol is provided in micronized form.

11. The method of claim 1, wherein the intestinal inflammation is irritable bowel syndrome.

12. The method of claim 1, wherein the intestinal inflammation is inflammatory bowel disease.

* * * * *